(12) United States Patent
Rönnberg et al.

(10) Patent No.: US 7,708,729 B2
(45) Date of Patent: *May 4, 2010

(54) WAIST BELT FOR ABSORBENT GARMENT

(75) Inventors: Peter Rönnberg, Mölndal (SE); Olle Carlbark, Kållered (SE); Björn Larsson, Billdal (SE)

(73) Assignee: SCA Hygiene Products AB, Gothenburg (SE)

( * ) Notice: Subject to any disclaimer, the term of this patent is extended or adjusted under 35 U.S.C. 154(b) by 547 days.

This patent is subject to a terminal disclaimer.

(21) Appl. No.: 10/270,686

(22) Filed: Oct. 16, 2002

(65) Prior Publication Data

US 2003/0032934 A1    Feb. 13, 2003

Related U.S. Application Data

(63) Continuation of application No. 10/005,144, filed on Dec. 7, 2001, now Pat. No. 6,500,163, which is a continuation of application No. 08/545,717, filed as application No. PCT/SE94/00426 on May 9, 1994, now Pat. No. 6,342,050.

(30) Foreign Application Priority Data

May 12, 1993   (SE) .................................. 9301630

(51) Int. Cl.
  *A61F 13/15*  (2006.01)
  *A61F 13/20*  (2006.01)
(52) U.S. Cl. ................. 604/392; 604/386; 604/393; 604/394

(58) Field of Classification Search ................. 604/386, 604/387, 326, 392–396
See application file for complete search history.

(56) References Cited

U.S. PATENT DOCUMENTS

| 3,587,580 A | | 6/1971 | Jones et al. |
| 3,860,003 A | * | 1/1975 | Buell .................... 604/385.25 |
| 4,964,860 A | | 10/1990 | Gipson |

(Continued)

FOREIGN PATENT DOCUMENTS

EP   0 287 388 A2   10/1988

(Continued)

OTHER PUBLICATIONS

Norwegian Patent Application No. 19954515—Extract from the files to the decision of Dec. 4,1998 in the First Division of the Patent Office.

(Continued)

*Primary Examiner*—Melanie J Hand
(74) *Attorney, Agent, or Firm*—Buchanan Ingersoll & Rooney PC

(57) ABSTRACT

The invention concerns a garment (1) comprising an absorbent section (2) and a waist belt (3) attached directly or indirectly thereto. The waist belt has two belt portions (7, 8) extending on either side of said absorbent section for securing to each other around a wearer of the garment The particular handling characteristics of the belt parts of the waist belt (3) are significantly improved by manufacturing a belt stiffness of between 25 g and 90 g as measured by the modified version of test ASTM D 4032-82 CIRCULAR BEND PROCEDURE.

26 Claims, 2 Drawing Sheets

U.S. PATENT DOCUMENTS

| | | | |
|---|---|---|---|
| 5,030,176 A | * | 7/1991 | Hodgetts .................... 474/261 |
| 5,052,872 A | * | 10/1991 | Hunder et al. ................. 412/6 |
| 5,300,055 A | | 4/1994 | Buell |
| H1440 H | | 5/1995 | New et al. |
| H001440 H | * | 5/1995 | New et al. .................... 604/386 |
| 5,509,914 A | | 4/1996 | Osborn, III |
| 5,607,416 A | | 3/1997 | Yomamoto et al. |
| 5,706,524 A | | 1/1998 | Herrin et al. |
| 5,904,673 A | | 5/1999 | Roe et al. |
| 6,086,571 A | | 7/2000 | Guevara et al. |
| 6,500,163 B2 | | 12/2002 | Rönnberg et al. |
| 6,540,731 B2 | | 4/2003 | Magnussson et al. |
| 2001/0034511 A1 | | 10/2001 | Hermansson et al. |
| 2002/0091367 A1 | | 7/2002 | Kusibojoska et al. |

FOREIGN PATENT DOCUMENTS

| | | |
|---|---|---|
| EP | 0336578 A1 | 10/1989 |
| EP | 0 409 307 A2 | 1/1991 |
| EP | 0 486 006 A2 | 5/1992 |
| EP | 0 528 282 A2 | 8/1992 |
| EP | 0 605 012 A1 | 7/1994 |
| EP | 0 729 329 B | 3/1999 |
| EP | 1 216 679 A2 | 6/2002 |
| FR | 2 586 558 | 3/1987 |
| GB | 1 200 177 | 7/1970 |
| GB | 2 216 774 A | 10/1989 |
| GB | 2257895 | 1/1993 |
| GB | 2 283 661 A | 5/1995 |
| TW | 233473 | 11/1994 |
| WO | WO 91/08725 | 6/1991 |
| WO | 94/26222 | 11/1994 |
| WO | 94/26224 | 11/1994 |
| WO | 94/26225 | 11/1994 |
| WO | 97/33547 | 9/1997 |
| WO | 97/34037 | 9/1997 |
| WO | 98/37847 | 9/1998 |
| WO | 99/21522 | 5/1999 |
| WO | 99/37263 | 7/1999 |
| WO | 00/27330 | 5/2000 |
| WO | 01/00129 A1 | 1/2001 |
| WO | 01/74283 A1 | 10/2001 |
| WO | 02/03901 A1 | 1/2002 |
| WO | 02/05739 A1 | 1/2002 |
| WO | 02/22061 A1 | 3/2002 |
| WO | 02/22062 A1 | 3/2002 |
| WO | 02/22063 A1 | 3/2002 |
| WO | 02/22064 A1 | 3/2002 |
| WO | 02/22065 A1 | 3/2002 |
| WO | 02/24134 A1 | 3/2002 |
| WO | 02/24135 A1 | 3/2002 |
| WO | 02/49567 A1 | 6/2002 |
| WO | 02/49568 A1 | 6/2002 |

OTHER PUBLICATIONS

Norwegian Patent Application No. 19954515—Translation of the Second Division Decision of Sep. 27, 2000; Second Division Case No. 6979.

* cited by examiner

WAIST BELT FOR ABSORBENT GARMENT

This application is a continuation of U.S. application Ser. No 10/005,144, filed on Dec. 7, 2001, now U.S. Pat. No. 6,500,163 which is a continuation of U.S. application Ser. No. 08/545,717, filed on Nov. 7, 1995 now U.S. Pat. No. 6,342,050, which was a national stage filing under 35 U.S.C. §371 of the International Application No. PCT/SE94/00426 filed on 9 May 1994, which International Application was published by the International Bureau in English on 24 Nov. 1994.

FIELD OF THE INVENTION

The invention relates to a garment comprising an absorbent section and a waist belt attached directly or indirectly thereto, said waist belt having two belt portions extending on either side of said absorbent section for securing to each other around a wearer of the garment, as defined in the preamble of claim 1.

BACKGROUND OF THE INVENTION

Absorbent garments of the above mentioned type are well known in the art.

The type of garment in question has a belt attached integrally with the absorbent garment portion and requires that, after fastening the belt around the waist with the attached end at the back of the wearer, the end not attached to the belt section should be passed through the wearer's legs and attached by some means of releasable attachment to the belt at the front. The means of releasable attachment could be a hook and loop (also called touch and close) type fastening means, for instance such as sold under the name "VELCRO".

Published application WO-A-91/08725 discloses an example of such a garment in one embodiment.

One of the problems recognised with such garments is the problems of handling the belt portions which project from either side of the absorbent portion of the integrated garment in such a way so as to be able to quickly and accurately take hold of the belt portions and fasten them together. However the belt material still needs to be cheap since it is integrated with a garment which together with the belt form a disposable unit.

Where the problem of incontinence is involved, it will be appreciated that persons suffering from this problem are often old and have physical handicaps of various types. As a consequence, they have more difficulty fastening the belt by themselves and often require the assistance of personnel for fitting the garments.

Thus there is a need to find for a solution which allows easy and correct fitting of the absorbent garment, particularly in the case of handicapped persons.

SUMMARY OF THE INVENTION

The aforementioned problems of handling are solved by the features of the belt according to claim 1.

The resultant belt of the garment is one which is not prone to excessive wrinkling which could be painful for the wearer and not too stiff which causes problems of cutting and abrasion itself. Additionally, a garment is achieved with a belt which can be made cheaply and is particularly suitable for adult incontinence applications.

Preferred features of the belt are defined in the dependent claims.

The flexure-resistance of a material sample is measured by its peak bending stiffness. Thus as defined in claim 1 and as disclosed in the sample testing method of EP-A-0 336 578, said testing equipment, procedure and calculations hereby being incorporated by reference, the peak bending stiffness is determined by a test modelled after the ASTM D 4032-82 CIRCULAR BEND PROCEDURE, the procedure being considerably modified and performed as indicated in EP-A-0 336 578.

The CIRCULAR BEND PROCEDURE is a simultaneous multi-directional deformation of a material in which one face of a specimen becomes concave and the other face becomes convex. The CIRCULAR BEND PROCEDURE gives a force value related to flexure-resistance, simultaneously averaging stiffness in all directions.

The tests were carried out on the belt of the present application using the apparatus from EP-A-0 336 578 necessary for the CIRCULAR BEND PROCEDURE which is a modified Circular Bend Stiffness Tester, having the following parts:

A smooth-polished steel plate platform which is 102.0× 102.0×6.35 millimeters having an 18.75 millimeter diameter orifice. The lap edge of the orifice should be at a 45 degree angle to a depth of 4.75 millimeters.

A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0,5 millimeter, the plunger being mounted concentrically with the orifice and having equal clearance on all sides. It should be noted that the needle point is merely to prevent lateral movement of the test specimen during testing. Therefore, if the needle-point, significantly adversely affects the test specimen (for example by puncturing an inflatable structure), than the needle-point should not be used. The bottom of the plunger should be set well above the top of the orifice plate. From this position, the downward stroke of the ball nose is to the exact bottom of the plate orifice. A force-measurement gauge and more specifically an Instron inverted compression load cell. The load cell has a load range of from 0.0 to 2000.0 grams. An actuator, and more specifically the Instron Model No. 1122, having an inverted compression load cell. The Instron 1122 is made by the Instron Engineering Corporation, Canton, Mass.

It should be noted that, whilst the term "absorbent garment" has been used particularly in conjunction with incontinence, and particularly adult incontinence, the invention is not limited to this particular use or any particular size or type of absorbent garment implied thereby and it is clear for the skilled man that such belts could be used with baby's or children's nappies (diapers) for example, merely by adapting the dimensions appropriately.

BRIEF DESCRIPTION OF THE DRAWINGS

The invention will now be explained in more detail with reference to certain non-limiting embodiments and with reference to the accompanying drawings, in which.

DETAILED DESCRIPTION OF PREFERRED EMBODIMENTS

Figure 1:
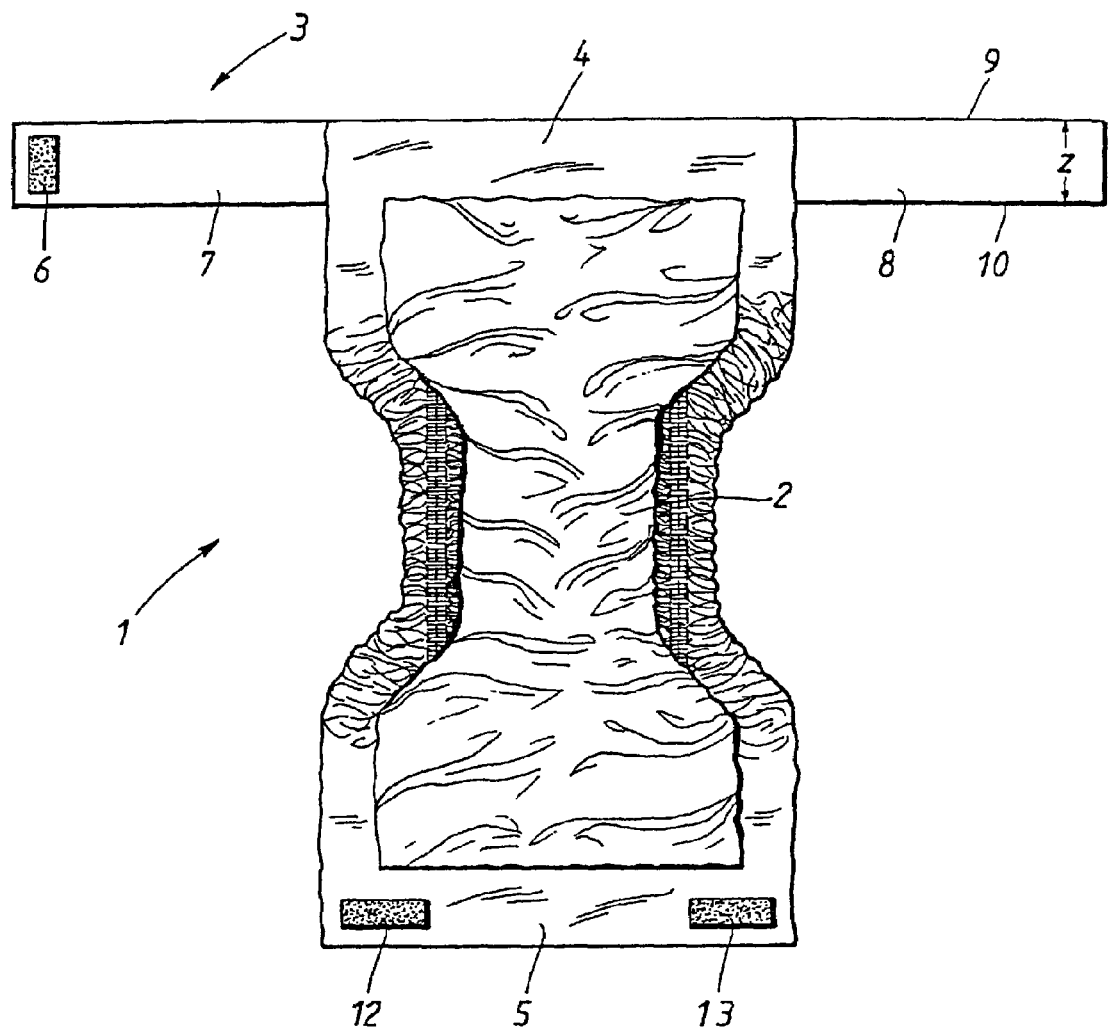
FIG. 1 depicts a garment including a belt according to the invention.

FIG. 1 shows a garment generally denoted 1 which consists of an absorbent portion 2 and a belt portion generally denoted 3.

The belt could be either one continuous belt 3 attached to the absorbent portion 2 at one end 4 thereof or could be two separate belt portions 7 and 8 each attached to a respective side of the end 4 (or 5). The manner of attachment per se is of no importance for the present application.

If it is desirable to impart elasticity to a belt made of two separate belt portions, it is conceivable that the end 4 of the absorbent portion 2 be elasticized.

The general appearance of the garment in the figures is known per se and thus no detailed explanation of all elements will be entered into. At one end of one part 7 of the belt 3 there is provided a flexible strip 6 of hook elements, of the hook and loop type of fastening means, which can either be secured to the belt part 8 (on the side not shown) or to a loop strip arranged on the belt part 8. Additional advantages, as explained below, will be obtained by particular dimensions and orientation of this strip. Whilst the belt is preferably substantially rectangular in shape comprising two laterally spaced longitudinal edges 9 and 10, between which the strip 6 will be attached, other shapes are conceivable. However, with a rectangular belt, the width of the belt should lie between 70 mm and 160 mm in adult incontinence applications.

Using such a belt, it is now possible to achieve good handling characteristics of the belt parts 7 and 8 even with the use of non-woven materials by selecting the range of stiffness according to the ASTM D 4032 modified test to lie between 25 g and 90 g. Below 25 g, the problem of wrinkling arises and this, as previously explained, is undesirable. Thus a free zone part of the belt (e.g. in the middle of one belt part 7) stiffness will lie in the stated range.

In particular according to the invention, the preferred range of stiffness lies between 30 g and 55 g and the best handling is obtained between 35 g and 50 g. Thus, in particular with the range of belts used for adult incontinence applications, the inventors have succeeded in achieving the optimum handling characteristics whilst still preventing wrinkling or stiff regions which cause discomfort.

A non-woven material is preferably used for either one or both sides of the belt, said non-woven material being of a type to which the hook elements of the strip 6 can releasable attach. By use of a non-woven material for the releasable attachment surface of the belt it is possible to achieve particularly favourable peel strength and shear strength combinations, which give a peel strength down to 0.1-2.0 $Ncm^{-1}$, preferably as low as 0.2-0.8 $Ncm^{-1}$, and a shear strength greater than 1 $Ncm^{-2}$, though preferably greater than 15 $Ncm^{-2}$ and normally greater than 20 $Ncm^{-2}$. The use of non-woven material is of course advantageous since it will be cheaper than woven material and thus more suitable to disposable garments. Such values are also valid for the attachment of strips 12 and 13 on end 5 of the garment which are attached to the non-shown side of the belt after fastening of the belt and passing through the wearer's legs.

The optimal handling characteristics which have now been achieved can of course thus be maintained even when using an inner side material for the belt part which is of absorbent material, preferably of non-woven sort, without increasing the cost to greater than prior art solutions using non-lined belts.

Since comfort of the wearer is a particularly important consideration in this field and in particular to fitting of the belt, it has been shown advantageous to adopt a particular placement of the hook element strips for fastening the belt together. Thus in order to reduce, to a great extent the possibility of the hook element strips contacting the wearer's waist due to incorrect fitting of the belt, or for the case where the waist of the user increases dimension, the hook element strip or strips are made of such a length and width and are positioned with such an orientation so as to avoid this.

Figure 2A:
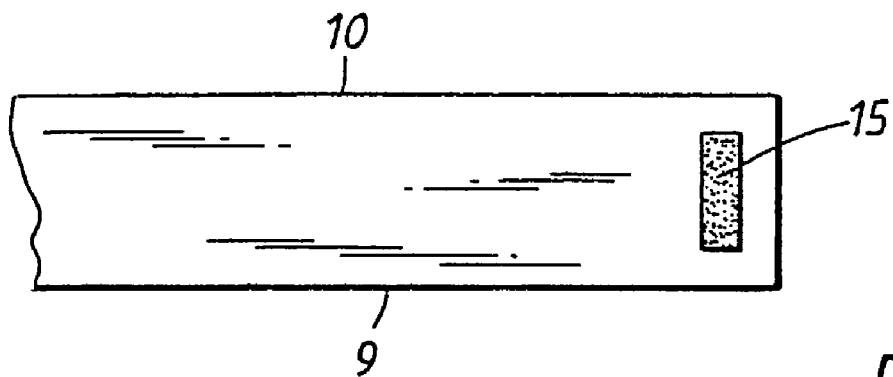
FIGS. 2A-2C show various attachment means used in accordance with fastening the belt of the present invention.

As can be seen from FIG. 2, showing three possible strip embodiments 15, 16 and 17, the distance between the outer edges of the strip(s) is spaced at a distance from each edge 9, 10 of the belt. In this way, when the belt is fitted, if slightly angled or not correctly overlapped, the hook elements will not project beyond the edge of the belt and thus will not contact the wearer's body.

Figure 2B:
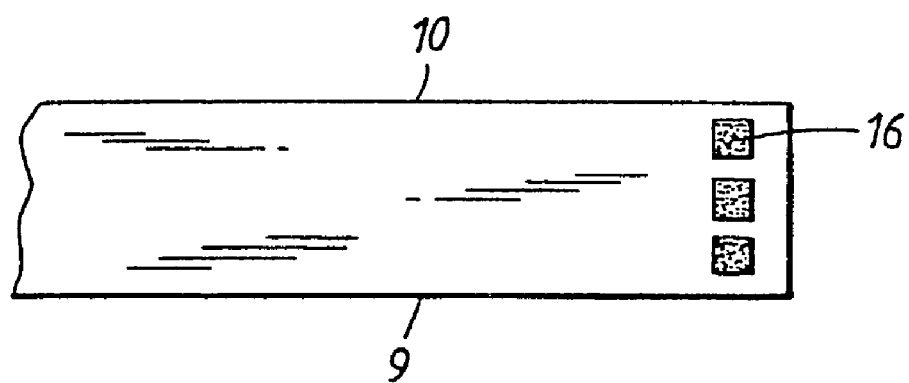
Figure 2C:
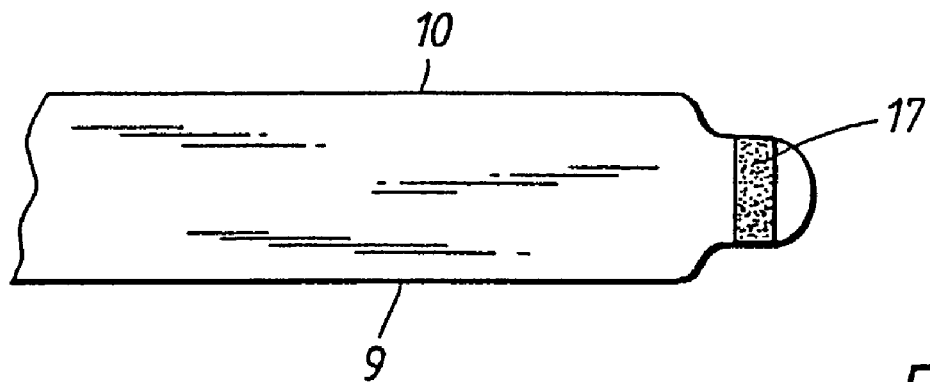

As can be seen, the strips are generally elongate, or in the case of a series of strips 16 as in FIG. 2(b), the series of strips is elongate. Preferably a ratio of greater than 2:1 elongation is used and even more preferably an elongation ration of over 3:1. Thus to achieve the afore-mentioned advantages it is preferable to lay the strips with their larger dimension across the belt width, as depicted, and to give the strips a dimension such that the larger dimension has a length of between 25% and 75% of the width (z) of the main area of the belt. By width of the belt, is hereby meant the width of the belt at the zone where the strip(s) 15, 16 and 17 will attach. Thus in the embodiment of FIG. 2(c), although the strip 17 extends entirely across the reduced portion of the belt, the strip still lies within the stated range. In particular it has been found particularly advantageous to use a strip with a length which is less than 60% or even more preferable less than 50%. Due to the shear strength which can be achieved by the use of non-woven materials as the belt attachment surface, it is also easy to acquire adequate shear strength with only minimal attachment area.

Additionally, with the choice of belt stiffness as claimed it is further also possible to avoid wrinkling occurring from attachment strips even when using smaller strip dimensions.

Whilst particular embodiments of the invention have been described above, it is to be understood that these are in no way limiting for the scope of the invention which is defined by the claims appended hereto.

Additionally, it will be understood by the skilled man that, whilst not preferred, the belt stiffness range can be used for non-integral belt applications also, for example where an absorbent chassis is fitted to the belt, by releasably attachable means.

The invention claimed is:

1. A garment comprising an absorbent section and a waist belt attached directly or indirectly thereto, said waist belt having two belt portions extending on either side of said absorbent section for securing to each other around a wearer of the garment, at least a portion of said waist belt having a stiffness of between 25 g and 90 g as measured by the modified version of test ASTM D 4032-82 CIRCULAR BEND PROCEDURE.

2. The garment according to claim 1, wherein said waist belt has a width of between 70 mm and 160 mm.

3. The garment according to claim 1, wherein said waist belt consists of only one non-woven material piece.

4. The garment according to claim 1, wherein the stiffness of the waist belt, as measured by the modified version of test ASTM D 4032-82 CIRCULAR BEND PROCEDURE, is between 30 g and 55 g.

5. The garment according to claim 1, wherein the stiffness of the waist belt, as measured by the modified version of test ASTM D 4032-82 CIRCULAR BEND PROCEDURE, is between 35 g and 50 g.

6. The garment according to claim 1, wherein the absorbent section, at an end remote from the end at which the belt is attached, is provided with hook element strips of a hook and loop type fastener for attachment of said remote end to the waist belt at spaced locations, and a connection of said hook element strips to said waist belt has a shear strength of 1 $Ncm^{-2}$, or more, and a peel strength of between 0.1-2.0 $Ncm^{-1}$.

7. The garment according to claim 1, wherein the absorbent section, at an end remote from the end at which the belt is attached, is provided with hook element strips of a hook and loop type fastener for attachment of said remote end to the waist belt at spaced locations, and a connection of said hook element strips to said waist belt has a shear strength of 15 $Ncm^{-2}$, or more, and a peel strength of between 0.2-0.8 $Ncm^{-1}$.

8. The garment according to claim 1, wherein the absorbent section, at an end remote from the end at which the belt is attached, is provided with hook element strips of a hook and loop type fastener for attachment of said remote end to the waist belt at spaced locations, and a connection of said hook element strips to said waist belt has a shear strength of 1 $Ncm^{-2}$, or more, and a peel strength of between 0.2-0.8 $Ncm^{-1}$.

9. The garment according to claim 1, wherein the absorbent section, at an end remote from the end at which the belt is attached, is provided with hook element strips of a hook and loop type fastener for attachment of said remote end to the waist belt at spaced locations, and a connection of said hook element strips to said waist belt has a shear strength of 15 $Ncm^{-2}$, or more, and a peel strength of between 0.1-2.0 $Ncm^{-1}$.

10. The garment according to claim 1, wherein one of said two belt portions has a hook element attachment strip attached thereto for securing one belt portion to the other belt portion, said attachment strip being elongate and lying with its larger dimension in the belt width direction whereby said larger dimension has a length of between 25% and 75% of the belt width.

11. The garment according to claim 1, wherein said waist belt is a single continuous belt attached to said absorbent section and the two belt portions each comprise ends of the single continuous belt extending from a respective side of said absorbent section.

12. The garment according to claim 1, wherein the portion of the waist belt is at a middle of one belt portion extending on one side of said absorbent section.

13. A garment comprising a garment portion and a waist belt attached directly or indirectly thereto, wherein the waist belt is a separately formed piece that is not integrally formed with the garment portion, said waist belt having two belt portions extending on either side of said garment portion for securing to each other around a wearer of the garment, at least a portion of said waist belt having a stiffness of between 25 g and 90 g as measured by the modified version of test ASTM D 4032-82 CIRCULAR BEND PROCEDURE.

14. The garment according to claim 13, wherein said waist belt has a width of between 70 mm and 160 mm.

15. The garment according to claim 13, wherein said waist belt consists of only one non-woven material piece.

16. The garment according to claim 1, wherein the stiffness of the waist belt, as measured by the modified version of test ASTM D 4032-82 CIRCULAR BEND PROCEDURE, is between 30 g and 55 g.

17. The garment according to claim 13, wherein the stiffness of the waist belt, as measured by the modified version of test ASTM D 4032-82 CIRCULAR BEND PROCEDURE, is between 35 g and 50g.

18. The garment according to claim 13, wherein the garment portion, at an end remote from the end at which the belt is attached, is provided with hook element strips of a hook and loop type fastener for attachment of said remote end to the waist belt at spaced locations, and a connection of said hook element strips to said waist belt has a shear strength of 1 $Ncm^{-2}$, or more, and a peel strength of between 0.1-2.0 $Ncm^{-1}$.

19. The garment according to claim 13, wherein the garment portion, at an end remote from the end at which the belt is attached, is provided with hook element strips of a hook and loop type fastener for attachment of said remote end to the waist belt at spaced locations, and a connection of said hook element strips to said waist belt has a shear strength of 15 $Ncm^{-2}$, or more, and a peel strength of between 0.2-0.8 $Ncm^{-1}$.

20. The garment according to claim 13, wherein the garment portion, at an end remote from the end at which the belt is attached, is provided with hook element strips of a hook and loop type fastener for attachment of said remote end to the waist belt at spaced locations, and a connection of said hook element strips to said waist belt has a shear strength of 1 $Ncm^{-2}$, or more, and a peel strength of between 0.2-0.8 $Ncm^{-1}$.

21. The garment according to claim 13, wherein the garment portion, at an end remote from the end at which the belt is attached, is provided with hook element strips of a hook and loop type fastener for attachment of said remote end to the waist belt at spaced locations, and a connection of said hook element strips to said waist belt has a shear strength of 15 $Ncm^{-2}$, or more, and a peel strength of between 0.1-2.0 $Ncm^{-1}$.

22. The garment according to claim 13, wherein one of said two belt portions has a hook element attachment strip attached thereto for securing one belt portion to the other belt portion, said attachment strip being elongate and lying with its larger dimension in the belt width direction whereby said larger dimension has a length of between 25% and 75% of the belt width.

23. The garment according to claim 13, wherein said waist belt is a single continuous belt attached to said garment portion and the two belt portions each comprise ends of the single continuous belt extending from a respective side of said garment portion.

24. The garment according to claim 13, wherein the portion of the waist belt is at a middle of one belt portion extending on one side of said garment portion.

25. The garment according to claim 13, said garment portion being delimited by opposed longitudinal edges and opposed transverse edges, wherein the two belt portions are two separately formed pieces that are attached to said garment portion at the longitudinal edges.

26. The garment according to claim 1, said absorbent section being delimited by opposed longitudinal edges and opposed transverse edges, wherein the two belt portions are two separately formed pieces that are attached to said absorbent section at the longitudinal edges.

* * * * *